United States Patent [19]

Barber

[11] Patent Number: 4,541,423
[45] Date of Patent: Sep. 17, 1985

[54] DRILLING A CURVED HOLE

[76] Inventor: Forest C. Barber, 2925 Race St., Fort Worth, Tex. 76111

[21] Appl. No.: 458,625

[22] Filed: Jan. 17, 1983

[51] Int. Cl.[4] .............................................. A61F 5/04
[52] U.S. Cl. ........................... 128/92 E; 128/92 EB; 128/305.1
[58] Field of Search ............ 128/92 E, 92 EB, 92 R, 128/303 R, 305, 305.1

[56] References Cited

U.S. PATENT DOCUMENTS 4,265,231  5/1981  Scheller, Jr. et al. ............ 128/92 E
4,312,337  1/1982  Donohue ........................ 128/92 E Primary Examiner—Gene Mancene
Assistant Examiner—C. W. Shedd
Attorney, Agent, or Firm—Peter J. Murphy

[57] ABSTRACT

Drilling apparatus for attachment to a rotary motor includes a flexible shaft confined in an elongated tubular sheath. The sheath is formed from a semi-rigid material which is bendable to a desired curvature, at the use site to select the curvature of the drilled hole, and which is rigid enough to retain that curvature in use. A drilling bit is fixed to one end of the flexible shaft, and includes a shank coacting with the distal end of the sheath to rotationally guide the drilling bit. The flexible shaft projects from the sheath at the proximal end so that both components may be secured to a drilling motor which is manipulated to guide the sheath while rotating the cutting bit. The sheath may remain in the drilled hole temporarily as a liner to guide the passage therethrough of a relatively stiff wire or other filamentary member.

16 Claims, 7 Drawing Figures

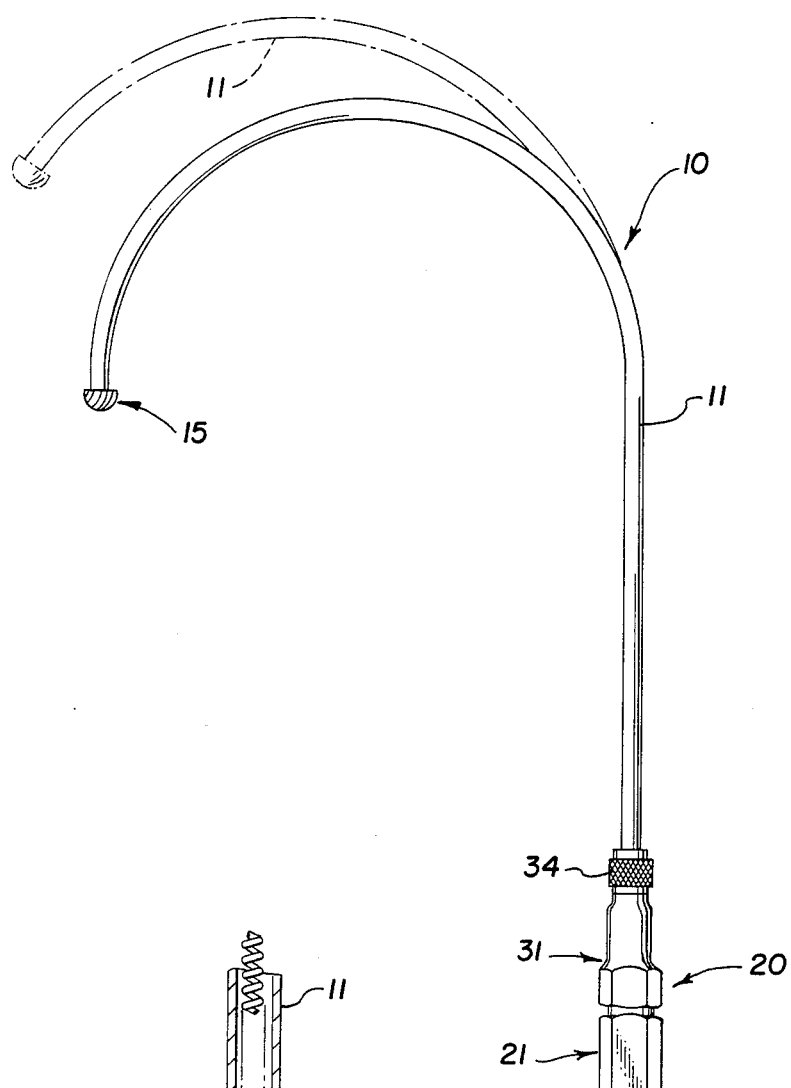
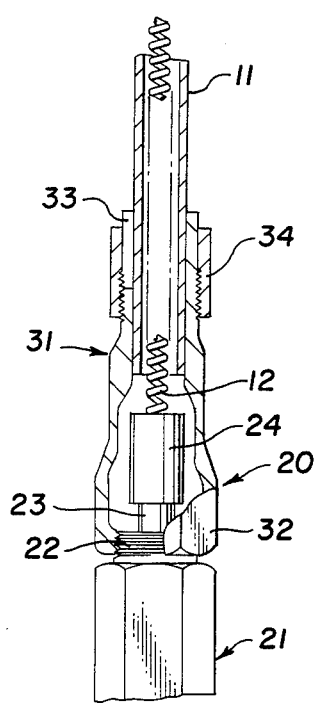
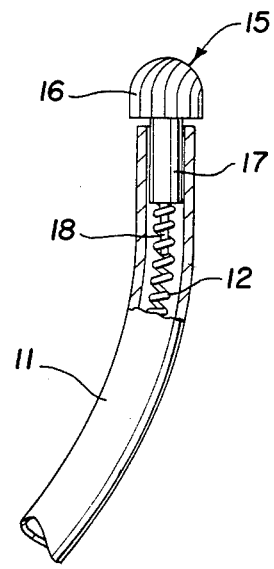
Fig. 1
Fig. 2
Fig. 3

DRILLING A CURVED HOLE

BACKGROUND AND SUMMARY OF THE INVENTION

This invention relates to an apparatus and method for drilling a hole or bore of selected curvature through a hard substance, where the curvature is selected and effected at the use site; and more particularly to a method and apparatus for drilling such a hole through bone to enable the securing thereto of wires or sutures for example.

In the field of orthopedic surgery, it frequently occurs that a hole must be drilled through bone to enabling the securing of a filamentary member to the bone. Such holes may be necessary, for example, to secure a ligament to a bone, or to immobilize two adjacent bones either temporarily or permanently. The filamentary members used for this purpose may be thread type sutures or may be wire for example.

For many of these procedures, a straight through hole may not be suitable for the intended purpose; and furthermore may be difficult or impossible to drill in the desired relation to the member or tissue which is to be secured to the bone. A common approach to the problem is to drill two straight intersecting holes, at appropriate angles to each other. One problem associated with this is that bone is a difficult material to drill since the drills tend to wander, so that achieving the intersecting point may be somewhat difficult. Another problem associated with this technique is that if the angle of the two holes is too acute, the threading of a suture needle or of a wire may be difficult.

It may be much preferred, in some instances, to be able to drill a curved hole or bore through the bone in one continuous sweep. Furthermore, it may be desirable to be able to change very quickly the radius of curvature of the hole to be drilled. This invention is concerned with an apparatus and a method for accomplishing these purposes, the apparatus being an improvement of apparatus described in Scheller, Jr., et al, U.S. Pat. No. 4,265,231, issued May 5, 1981.

An object of this invention is to provide novel apparatus for drilling a curved hole or bore.

Another object of this invention is to provide such apparatus wherein the radius of curvature may be changed readily.

A further object of this invention is to provide such apparatus wherein a portion of the drilling apparatus may be used as a hole liner after the drilling is completed.

Still another object of this invention is to provide a novel method for drilling a curved hole or bore.

A still further object of this invention is to provide such novel method enabling the ready threading of a filamentary member through the drilled hole.

Another object of this invention is to provide a novel apparatus and method for drilling a curved hole enabling the selection of the radius of curvature of the hole, to take advantage of the sculpture of the substance to be drilled or to best adapt the hole to the intended purpose.

These objects are accomplished in an attachment for a rotary motor which includes a flexible drive shaft confined within an enclosing tubular sheath. The sheath is fabricated from a semi-rigid material, and has one end configured to be nonrotatably coupled to the rotary motor. The flexible drive shaft has means at its proximal end for coupling to the output shaft of the rotary motor, and has a dissecting tool fixed to its distal end. The dissecting tool is guided for rotation by the tubular sheath, and has an outer diameter slightly larger than that of the sheath. The proximal end of the flexible shaft is dimensioned to pass through the sheath to enable removal of the dissecting tool and shaft from the sheath.

These objects are also accomplished in a method which includes the following steps. A rotary drilling tool is driven by means of a flexible shaft. The flexible shaft is confined in a tubular guiding sheath which is formable to a selected curvature, the sheath having a smaller outer diameter than the drilling tool. The assembly is guided through the material to be drilled, with the sheath following the drilling tool. The tool and attached flexible shaft may be withdrawn from the sheath so that the sheath may be used as a liner for the drilled hole.

The novel features and the advantages of the invention, as well as additional objects thereof, will be understood more fully from the following description when read in connection with the accompanying drawings.

DRAWINGS

FIG. 1 is a side view of drilling apparatus according to the invention attached to a rotary motor;

FIG. 2 is a fragmentary view, partially in axial section, illustrating the attachment of the drilling apparatus to the rotary motor;

FIG. 3 is a fragmentary view, partially in axial section, illustrating the distal end of the drilling apparatus including the drilling bit;

DESCRIPTION OF THE PREFERRED EMBODIMENTS

Figure 4:
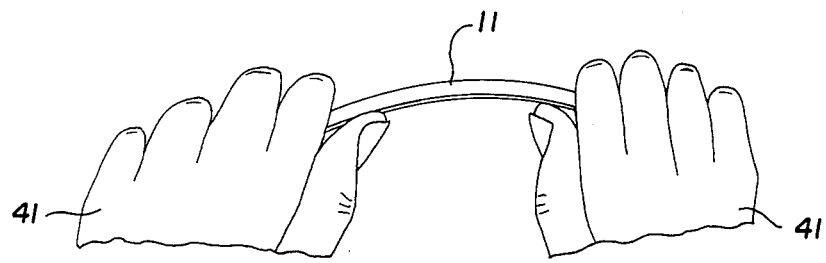
FIG. 4 is a view illustrating the manual bending of a sheath.

FIG. 1 of the drawing illustrates the assembly of drilling apparatus 10 according to the invention assembled with a suitable drive motor assembly 20. Referring to all of the figures, the drilling apparatus 10 includes an elongated tubular sheath or cannula 11 which encloses and confines an elongated flexible drive shaft 12. A drilling bit 15 is fixed to the distal end of the drive shaft 12; and the drilling burr of this bit is exposed at the distal end of the sheath 11. At the proximal end of the sheath and flexible shaft assembly, the shaft projects from the sheath to enable coupling to the drill motor drive shaft as will be described.

The sheath 11 is a tubular member of uniform cross section and is fabricated from a suitable metal or other material which has the characteristic of semi-rigidity. While the sheath 11 must have a certain degree of rigidity to enable the guiding of the drilling assembly through the bone or other material to assure a curved hole or bore, it is also desirable that the sheath be readily bendable by the user to enable the user to select the desired radius of curvature, and to immediately change that radius of curvature should that be desired. Accordingly, the material of the sheath has the characteristic that it can be bent or formed by the user into the desired curvature, and will retain that preselected curvature during the drilling operation. In addition to changing the radius of curvature, the user may wish to select or change the plane of the curved distal end of the sheath relative to the linear proximal end which is coupled to the drill motor; and this is readily accomplished by additional bending of the sheath, by the user at the use site, in a plane which is different from that of the curved distal end. It is seen then that the surgeon, or other user, of the apparatus of this invention can either minutely or radically change the shape of the sheath at will and in any plane he chooses. FIG. 4 of the drawing illustrates the manual bending of the sheath 11 by the hands 41 of a user of the apparatus. The term "semi-rigid", as used in this specification, is understood to refer to a sheath having the above described characteristic.

The flexible drive shaft 12 may have any suitable configuration; and is illustrated in the drawing as consisting of a coil spring which may be fabricated from any suitable material such as stainless steel. While the spring is illustrated in the drawing with open turns or coils, it may be preferable that the turns be contiguous to each other, in the normal coiled relationship, to assure stability of length of the drive shaft.

As best seen in FIG. 3 the drilling bit 15 may include an enlarged cutting head or burr 16, having a maximum outer diameter slightly larger than the outer diameter of the sheath 11 to enable the sheath to readily follow the bit through the drilled hole. The bit further includes a stepped shank having an intermediate larger diameter portion 17 and a smaller diameter end portion 18. The outer diameter of the intermediate shank portion 17 is only slightly smaller than the inner diameter of the sheath so that this shank portion and sheath have a coacting journal-bearing relationship to rotationally confine and guide the drilling bit 15. The diameter of the shank end portion 18 may be approximately the same as the inner diameter of the flexible shaft spring 12 so that the shank may be received within the spring to secure the drilling bit thereto. The spring may be secured to this shank portion 18 by any suitable means such as brazing for example.

The outer diameter of the flexible shaft 12 is preferably significantly smaller than the inner diameter of the sheath 11 to provide adequate clearance for free rotation of the shaft within the sheath and to minimize heat buildup due to friction.

The diameters of the several components of the above described drilling apparatus will be determined principally by the size of the hole which it is desired to drill. By way of example, the outer diameter of the sheath 11 may range from ⅛ to 5/16 inch with the other components being sized accordingly.

The motor assembly 20, as illustrated in the drawings, includes a high speed pneumatic drill motor 21 and an associated collet housing 31. The drill motor 21, illustrated fragmentarily in the drawings, includes a housing which is hexagonal in cross section and which is provided with a threaded pin 22 at one end surrounding the motor output shaft 23. A chuck 24 is associated with the motor output shaft for the purpose of securing the shaft of any implement to be driven, in this case the proximal end of the flexible shaft 12. The collet housing 31 has a hex shaped portion 32 at one end which is provided with a threaded box for coaction with the threaded pin 22 of the drill motor. The threads of the threaded pin and box are preferably left hand threads relative to right hand rotation of the motor output shaft.

The distal end of the collet housing 31 is generally tubular, having an inner diameter corresponding to the outer diameter of the sheath 11. This distal end is provided with longitudinal slots 33 thereby providing collet fingers which may be compressed into binding engagement with the sheath 11 by means of a collet nut 34; and in this manner the sheath 11 is nonrotatably coupled to the collet housing 31 and therefore to the drill motor 21.

Figure 6:
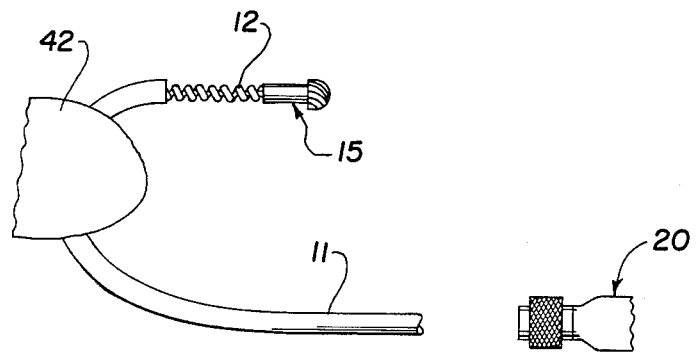
FIG. 6 is a view illustrating the separation of the motor assembly from the sheath and the withdrawal of the bit and flexible shaft from the sheath.

In orthopedic surgery, where metallic wire or other relatively stiff filamentary material is to be passed through the drilled hole, it may be desirable to leave the sheath within the drilled hole temporarily to facilitate the threading of that wire or relatively stiff filament. For this purpose, the drill motor assembly may be readily removed from the drilling apparatus by releasing the collet 33, 34 and by releasing the chuck 24, and then withdrawing the drill bit and shaft assembly from the distal end of the sheath. FIG. 6 illustrates the separation of the motor assembly 20 from the sheath 11, and the partial withdrawal of the bit 15 and shaft 12 from the sheath. The sheath then functions as a liner for the drilled hole to enable the ready threading or passing of the wire or filament; and after the wire has been passed through the hole the sheath may be withdrawn.

Figure 5:
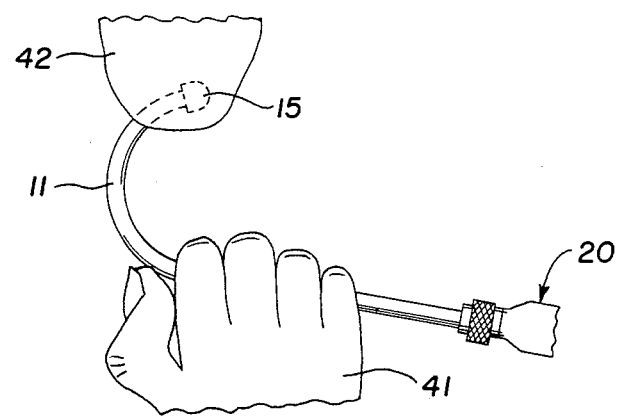
FIG. 5 is a view illustrating the manual guiding of a drilling apparatus.

The above described drilling apparatus enables the practice of a method for drilling a curved hole which includes the following steps. A rotary drilling tool is driven by means of a flexible shaft having the tool fixed to its distal end. The flexible shaft is enclosed in a semi-rigid tubular guiding sheath formable to a selected curvature by the user. The drilling tool is advanced through the hole by means of the guiding sheath while the flexible shaft is rotatably driven. The advancing and guiding of the bit 15 and sheath 11 through the bone 42 by the hand 41 of a user, is illustrated in FIG. 5. The drilling tool is rotationally supported at the distal end of the sheath to maintain axial alignment of the tool and sheath.

Figure 7:
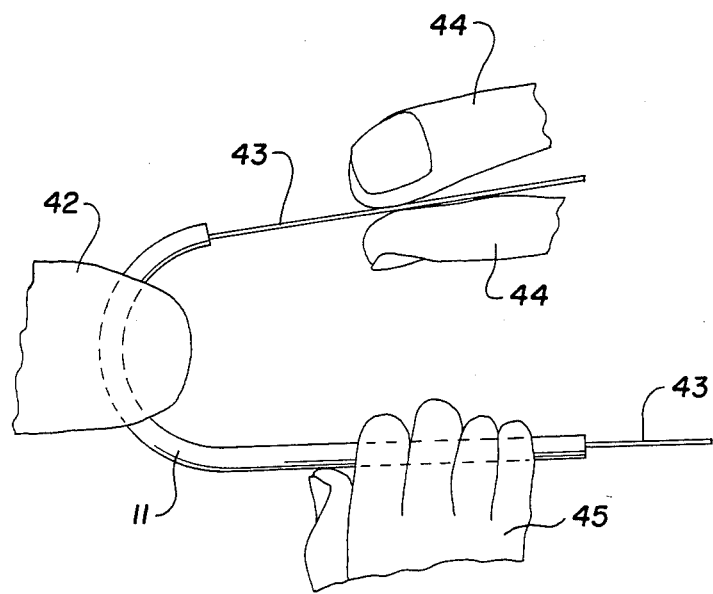
FIG. 7 is a view illustrating the removal of a sheath from a curved hole while retaining the filament in the hole.

The described apparatus also enables utilization of a method for threading a filamentary member through the drilled hole which includes the following steps. After the drilling of the hole, the drilling tool and associated flexible shaft are withdrawn from the sheath whereby the sheath provides a smooth liner for the drilled hole. A relatively stiff filamentary member is then passed readily through the lined curved hole. After the leading end of the filamentary member emerges from the curved hole and liner, that leading end may be grasped or otherwise secured while the sheath is removed from the hole, with the filamentary member then remaining in the desired relation relative to the drilled bone. FIG. 7 of the drawing illustrates the grasping of a filament 43 by the fingers 44 of one hand of the user (or of one person) while the fingers 45 of the user's other hand (or of another person) are grasping the sheath 11. In this manner the filament may first be threaded through the sheath, and the sheath may then be withdrawn from the hole drilled in the bone 42 by the fingers 45, while the fingers 44 retain the hold on the filament 43.

What has been described is a unique apparatus and method for drilling a curved hole, particularly for drilling a curved hole in bone in connection with orthopedic surgery.

A particular feature of the invention is that the confining sheath for the flexible shaft is formed of a semi-rigid material enabling the user to form the apparatus to the desired radius of curvature at the time of use. This may be of particular advantage in a surgical operation situation wherein the preferred radius of curvature for the hole to be drilled may not be ascertainable prior to the time the hole is to be drilled.

An advantage of the invention is that the sheath of the drilling apparatus may be left in the hole temporarily to provide a liner for the curved hole and facilitate the threading or passing through that hole a relatively stiff filamentary member such as metallic wire.

A further advantage of the invention is that it enables the preselection of the radius of curvature of the hole to be drilled, to take advantage of the sculpture of the substance being drilled and to adapt the drilled hole to the intended purpose.

While the preferred embodiments of the invention have been illustrated and described, it will be understood by those skilled in the art that changes and modifications may be resorted to without departing from the spirit and scope of the invention.

What is claimed is:

1. An attachment for a rotary motor for drilling curved holes in bone tissue comprising
    an elongated flexible drive shaft havaing a proximal end configured to be coupled to a rotary drive motor, and having a rotary drilling tool fixed to the distal end of the drive shaft;
    a semi-rigid tubular sheath, intentionally manually deformable to a selected curvature by the user, enclosing and guiding said flexible drive shaft and adapted to be non-rotatably coupled at one end to said rotary drive motor;
    said drilling tool having an outer diameter slightly larger than that of said sheath; and said shaft proximal end being dimensioned to pass through said sheath to enable removal of said drilling tool and shaft from said sheath.

2. An attachment as set forth in claim 1 further comprising
    said sheath being formable by the user to a selected radius of curvature, and having a stiffness sufficient to maintain the selected radius of curvature during the operation thereof.

3. An attachment as set forth in claim 2 further comprising
    said shaft having an outer diameter significantly smaller than the inner diameter of said sheath to provide for free rotatation of said shaft within said sheath.

4. An attachment as set forth in claim 1 further comprising
    said drilling tool having a journal shank nonrotatably fixed to said flexible shaft; said shank having an outer diameter only slightly smaller than the inner diameter of said sheath whereby said sheath provides bearing support for said journal shank.

5. An attachment as set forth in claim 4 further comprising
    said flexible shaft having an outer diameter smaller than that of said journal shank, to provide clearance between said shaft and said enclosing sheath.

6. A method for drilling a curved hold in bone tissue comprising the steps
    driving a rotary drilling tool by means of a flexible shaft having said tool fixed to its distal end;
    enclosing said flexible shaft in a tubular guiding sheath intentionally formable by the user to a selected curvature;
    configuring said sheath to have an outer diameter smaller than that of said drilling tool;
    advancing said drilling tool through the material to be drilled by means of said sheath while rotatably driving said drilling tool.

7. A method as set forth in claim 6 including the step, prior to advancing said drilling tool, of manually forming said sheath to a desired curvature.

8. A method as set forth in claim 6 including the step of
    withdrawing said drilling tool and attached flexible shaft from said sheath, whereby said sheath provides a liner guide for the drilled hole.

9. A method as set forth in claim 8 including the steps of
    threading a filamentary member through said sheath within said hole; and
    withdrawing said sheath from said hole, leaving said filamentary member in place.

10. A method as set forth in claim 8 including the step of
    withdrawing said drilling tool and attached flexible shaft from said sheath, while said sheath remains within the drilled hole whereby said sheath provides said liner guide.

11. A method as set forth in claim 6 including the step of
    journaling said drilling tool within the distal end of said sheath.

12. A method as set forth in claim 6 including the steps of
    advancing said drilling tool through said material in one direction to complete a through curved hole; and
    withdrawing said drilling tool and attached flexible shaft from said sheath while said sheath remains in said hole, whereby said sheath provides a liner guide for said drilled hole.

13. A method as set forth in claim 12 including the steps of
    threading a filamentary member through said sheath within said hole; and
    withdrawing said sheath from said hole, leaving said filamentary member in place.

14. A method as set forth in claim 6 including the step,
    prior to advancing said drilling tool, of forming said sheath to a selected configuration at the use site.

15. A method as set forth in claim 14 including the step of
    said forming of said sheath including bending the distal end thereof to a selected radius of curvature.

16. A method as set forth in claim 15 including the step of
    said forming of said sheath including the bending of said sheath to orient the curved distal end in a selected plane relative to the linear proximal end thereof.

* * * * *